(12) United States Patent
Bringoltz et al.

(10) Patent No.: US 9,909,982 B2
(45) Date of Patent: Mar. 6, 2018

(54) PUPIL PLANE CALIBRATION FOR SCATTEROMETRY OVERLAY MEASUREMENT

(71) Applicant: KLA-Tencor Corporation, Milpitas, CA (US)

(72) Inventors: Barak Bringoltz, Rishon le Tzion (IL); Irina Vakshtein, Haifa (IL); Ofir Aharon, Yokneam Eililt (IL); Guy Ben Dov, Haifa (IL); Zeev Bomzon, Kiryat Tivon (IL)

(73) Assignee: KLA-Tencor Corporation, Milpitas, CA (US)

( * ) Notice: Subject to any disclaimer, the term of this patent is extended or adjusted under 35 U.S.C. 154(b) by 324 days.

(21) Appl. No.: 14/244,179

(22) Filed: Apr. 3, 2014

(65) Prior Publication Data

US 2014/0257734 A1    Sep. 11, 2014

Related U.S. Application Data

(63) Continuation of application No. PCT/US2014/022756, filed on Mar. 10, 2014.

(60) Provisional application No. 61/775,230, filed on Mar. 8, 2013.

(51) Int. Cl.
| | |
|---|---|
| *G01C 19/00* | (2013.01) |
| *G01N 21/47* | (2006.01) |
| *G03F 7/20* | (2006.01) |

(52) U.S. Cl.
CPC ..... *G01N 21/4785* (2013.01); *G03F 7/70633* (2013.01)

(58) Field of Classification Search
CPC .. G01N 21/4785; G01B 11/00; G03F 7/70633
See application file for complete search history.

(56) References Cited

U.S. PATENT DOCUMENTS

| | | | |
|---|---|---|---|
| 2008/0204690 A1* | 8/2008 | Berger | G03F 7/70216 355/67 |
| 2008/0239318 A1 | 10/2008 | Den Boef et al. | |
| 2009/0262362 A1* | 10/2009 | de Groot | G03F 7/70633 356/508 |
| 2010/0134786 A1* | 6/2010 | De Lega | G01B 9/023 356/73 |
| 2011/0102753 A1* | 5/2011 | Van De Kerkhof | G01N 21/4788 355/27 |
| 2011/0128512 A1* | 6/2011 | Pellemans | G03F 7/70633 355/27 |
| 2011/0178785 A1* | 7/2011 | Tinnemans | G01N 21/4785 703/2 |
| 2012/0013881 A1 | 1/2012 | Den Boef et al. | |

(Continued)

OTHER PUBLICATIONS

U.S. Appl. No. 14/161,398, filed Jan. 22, 2014.

*Primary Examiner* — Stephanie Bloss
(74) *Attorney, Agent, or Firm* — Suiter Swantz pc llo (57) ABSTRACT

Methods and calibrations modules are provided, for calibrating a pupil center in scatterometry overlay measurements. The calibration comprises calculating fluctuations from a first statistical figure of merit such as an average of an overlay signal per pixel at the pupil and significantly reducing, for example minimizing, the fluctuations with respect to a second statistical figure of merit thereof, such as a pupil weighted variance of the fluctuations.

18 Claims, 6 Drawing Sheets

(56) References Cited

U.S. PATENT DOCUMENTS

2012/0123581 A1* 5/2012 Smilde ............... G03F 7/70483
 700/105
2013/0044331 A1 2/2013 Manassen et al.

* cited by examiner

PUPIL PLANE CALIBRATION FOR SCATTEROMETRY OVERLAY MEASUREMENT

CROSS-REFERENCE TO RELATED APPLICATIONS

This application is filed under 35 U.S.C. § 120 and § 365(c) and is a continuation of PCT International Patent Application No. PCT/US2014/022756, filed Mar. 10, 2014, which application claims the benefit of U.S. Provisional Patent Application No. 61/775,230, filed Mar. 8, 2013, which applications are incorporated herein by reference in their entirety.

BACKGROUND OF THE INVENTION

1. Technical Field

The present invention relates to the field of metrology, and more particularly, to scatterometry overlay metrology.

2. Discussion of Related Art

Miscalibration of the pupil plane is a source of errors in scatterometry overlay metrology. Common methods calibrate the pupil plane by measuring a mirror-like calibration target and modeling the detected electromagnetic signal by solving the respective Maxwell equations.

SUMMARY OF THE INVENTION

One aspect of the present invention provides a method of calibrating a pupil center in scatterometry overlay measurements, which comprises calculating fluctuations from an average of an overlay signal per pixel at the pupil and minimizing the fluctuations with respect to a pupil weighted variance thereof.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Prior to the detailed description being set forth, it may be helpful to set forth definitions of certain terms that will be used hereinafter.

The term "minimizing" as used in this application refers to a significant reduction, i.e., a reduction that may be discerned in metrology results with respect to a non-calibrated measurement. An absolute minimum is not required and any significant reduction is within the scope of the invention.

The term "statistical figure of merit" as used in this application refers to any statistical function applied to pupil plane pixels or to any data or value referring to specific pupil plane pixels, such as a weighted average and calculated overlay values, respectively, as a non-limiting example.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
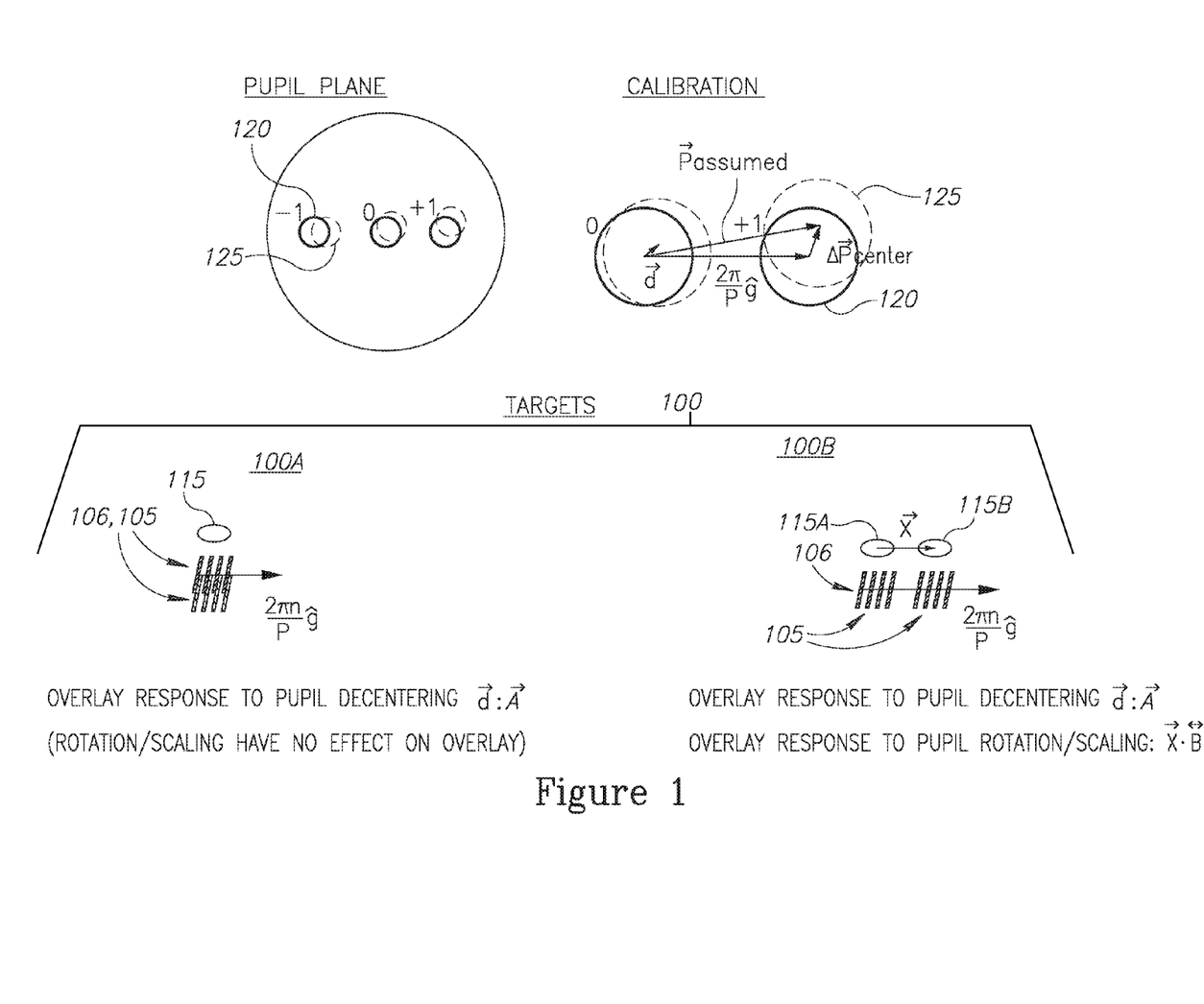
FIG. 1 is a high level schematic illustration of targets, the respective pupil plane images and the respective calibration variables, according to some embodiments of the invention.

FIG. 1 is a high level schematic illustration of targets 100, the respective pupil plane images and the respective calibration variables, according to some embodiments of the invention. FIG. 1 schematically illustrates two generic types of scatterometry overlay (SCOL) targets, namely a (standard) SCOL target (100A, left) having target cells 105 at different target layers 106 which are at least partially overlapping and side-by-side SCOL target (100B, right) having target cells 105 which are at least partially non-overlapping (in one or more layers). For each target 100A, 100B, a schematic view illustrates the radiation spots 115 which are generated by the respective target is schematically illustrated (one spot 115 for standard SCOL target 100A and two spots 115A, 115B interspaced by $\vec{X}$ for side-by-side SCOL target 100B). At the bottom, the pupil plane images are schematically illustrated as comprising diffraction orders −1, 0, +1 (from left to right in the bottom left image, orders 0 and +1 magnified at the bottom right image). Each order at the pupil plane illustration comprises an actual pupil image 125 of respective targets 100A, 100B and respective calibrated pupil images 120.

Methods for the calibration of the coordinates of detectors that are placed in the pupil plane are disclosed. Such calibration is important for measurements done with optical scatterometry. The methods are exemplified using the first order diffracted signals in overlay scatterometry measurement techniques. The methods may be applied to different SCOL target designs, with or without overlapping target cells and provide an accurate calibration of the pupil plane which enhances any type of metrology measurements, for example critical dimension (CD), width of layers, side wall angle, height of gratings, overlay, etc.

The disclosed methods overcome metrology errors resulting from miscalibration of the pupil plane and prevent a degradation of the metrology performance, manifested in tool induced shift (TIS) and its variance (TIS3S—tool induced shift 3-sigma—a variability value relating to the TIS). Moreover, the disclosed methods are superior to calibration methods which involve measuring a calibration target which is most often a mirror-like substrate with known properties, and modeling the detected electromagnetic signal by means of a solution of Maxwell equations. Such modeling includes, as parameters, the calibration degrees of freedom, and fitting of the model to the data fixes the calibration parameters, thereby completing the calibration of the pupil plane. However, these practiced methods involve problems in the modeling process, the accuracy and repeatability of which being restricted by the sensitivity of the signal to the calibration variables and by the approximation made by the numerical modeling engine used which is often limited by computational resources. In contrast, the disclosed methods do not involve electromagnetic modeling of the type described above, and provide very good sensitivity to the calibration parameters.

Without being bound by theory, the following model of the pupil plane image is used to exemplify the disclosed methods. The model itself does not limit the implementation of the methods but serves for illustrative purposes only. Model variables are schematically illustrated in a schematic manner in FIG. 1.

First, a transformation between the wave-vector coordinate $\vec{q}$ and the pupil plane coordinate $\vec{p}$ is defined in Equation 1.

$$\vec{q} = \vec{d} + \vec{\vec{B}} \vec{p} \qquad \text{Equation 1}$$

As Equation 1 shows, it is assumed that the transformation between the wave-vector coordinate and the pupil plane coordinate is linear. The vector $\vec{d}$ is the shift in the coordinate system (pupil decentering) and B is a 2×2 matrix that determines the relative scaling and rotation properties of the pupil plane grid. For orientation it is noted that $$\vec{q} = \frac{2\pi n}{P} \hat{g}$$

is a wave vector that corresponds to light arriving at the target with normal illumination and reflecting in the n-th diffraction order. It is also noted that this assumption is an illustrative simplification, and introduction of respective corrections for this assumption is part of the disclosed methods.

The overlay signal obtained at a pupil coordinate $\vec{p}$ and extracted from overlay target 100 using first order scatterometry overlay techniques can be written as in Equation 2.

$$OVL(\vec{p}, \vec{d}, \vec{\vec{B}}) = OVL_{real} + \vec{d} \cdot \vec{A}(\vec{p}) + \frac{P}{2\pi} \vec{X} \cdot \vec{\vec{B}} \cdot \Delta \vec{p}_{center} \qquad \text{Equation 2}$$

In Equation 2, P is the pitch of the grating, and $\hat{g}$ is the grating vector. $OVL_{real}$ is the overlay between target cells 105 of target 100, the vector $\vec{A}$ is the overlay linear response to the pupil decentering, and $\Delta \vec{p}_{center}$ is a vector connecting $\vec{p}_{assumed}$, which is the pupil point assumed to correspond to the center of the first diffraction order but deviating therefrom due to miscalibrations, and $$\frac{2\pi n}{P} \hat{g},$$

as formulated in Equation 3 (see also FIG. 1).

$$\Delta \vec{p}_{center} = \vec{p}_{assumed} - \frac{2\pi}{P} \hat{g} \qquad \text{Equation 3}$$

It is noted that the "center" subscript illustrates the fact that in the absence of miscalibrations, $\vec{p}_{assumed}$ corresponds to the center of the first diffraction order. Finally, $\vec{X}$ is the distance between the two radiation spots in case of side-by-side technologies, resulting from the non-overlapping of target cells 105 (see target 100B) and is zero for first order scatterometry overlay (SCOL) using overlapping targets (see target 100A). Therefore the last term $$\frac{P}{2\pi} \vec{X} \cdot \vec{\vec{B}}.$$

$\Delta \vec{p}_{center}$ in Equation 2 is present when using targets 100B with non-overlapping target cells 105 (side-by-side targets) and absent when using targets 100A with overlapping target cells 105 (e.g., as in grating-over-grating SCOL targets).

In side-by-side SCOL measurements, the linear response to $\vec{d}$ obeys Equation 4.

$$\vec{A}(\vec{p}) = \frac{P}{4\pi} \left[ \begin{array}{c} \{\vec{\nabla} \psi_{n=+1}^{g(1)}(\vec{z})\}_{\vec{z}=\vec{\vec{B}}\vec{p}-\frac{2\pi}{P}\hat{g}} + \{\vec{\nabla} \psi_{n=+1}^{g(1)}(\vec{z})\}_{\vec{z}=\vec{\vec{B}}(2\vec{p}_{assumed}-\vec{p})-\frac{2\pi}{P}\hat{g}} \\ - \{\vec{\nabla} \psi_{n=+1}^{g(2)}(\vec{z})\}_{\vec{z}=\vec{\vec{B}}\vec{p}-\frac{2\pi}{P}\hat{g}} - \{\vec{\nabla} \psi_{n=+1}^{g(2)}(\vec{z})\}_{\vec{z}=\vec{\vec{B}}(2\vec{p}_{assumed}-\vec{p})-\frac{2\pi}{P}\hat{g}} \end{array} \right] \qquad \text{Equation 4}$$

In Equation 4, $\psi_n^{g(i)}(\vec{k})$ is the phase that the wave vector $\vec{z}$ acquires when it is reflected from grating g(i) at diffraction order $\vec{\nabla}$ denotes the gradient of the function $\{\psi_{n=+1}^{g(1)}(\vec{z})\}$ with respect to $\vec{z}$. Importantly, simulations show that for a grating in the $\hat{g}$ direction, the vector $\vec{A}(\vec{p})$ has a very small projection onto the direction perpendicular to $\hat{g}$, as expressed in Equation 5.

$$|\vec{A} \hat{g}| << |\vec{A} \cdot \hat{g}|, \qquad \text{Equation 5}$$

From Equation 5 it follows that Equation 2 can be approximated by the following Equation 6.

$$OVL(\vec{p}, \vec{d}, \vec{\vec{B}}) = OVL_{real} + (\vec{d} \cdot \hat{g})(\vec{A}(\vec{p}) \cdot \hat{g}) + \frac{P}{2\pi} \vec{X} \cdot \vec{\vec{B}} \cdot \Delta \vec{p}_{center} \qquad \text{Equation 6}$$

It is noted that the term $$\frac{P}{2\pi}\vec{X}\cdot\overleftrightarrow{B}\cdot\Delta\vec{p}_{center}$$

in Equations 2 and 6 is independent of $\vec{p}$, and thus has zero coupling to the wafer reflectivity. As such it is a completely calibratable TIS source and does not contribute to TIS3S. This is in contrast to the term $(\vec{d}\cdot\hat{g})(\vec{A}(\vec{p})\cdot\hat{g})$ in Equations 2 and 6 which is pupil dependent and couples to the properties of the wafer reflectivity through its dependence on $\psi_n^{g(i)}(\vec{k})$ (as expressed in Equation 4). Indeed, simulations show that this TIS cause is an important contributor to the small, yet nonzero, TIS3S of side-by-side SCOL (targets 100B). Clearly, the latter term's dependence on the pupil coordinate and on the wafer reflectance is present also when using SCOL targets with overlapping cells (targets 100A).

Figure 2:
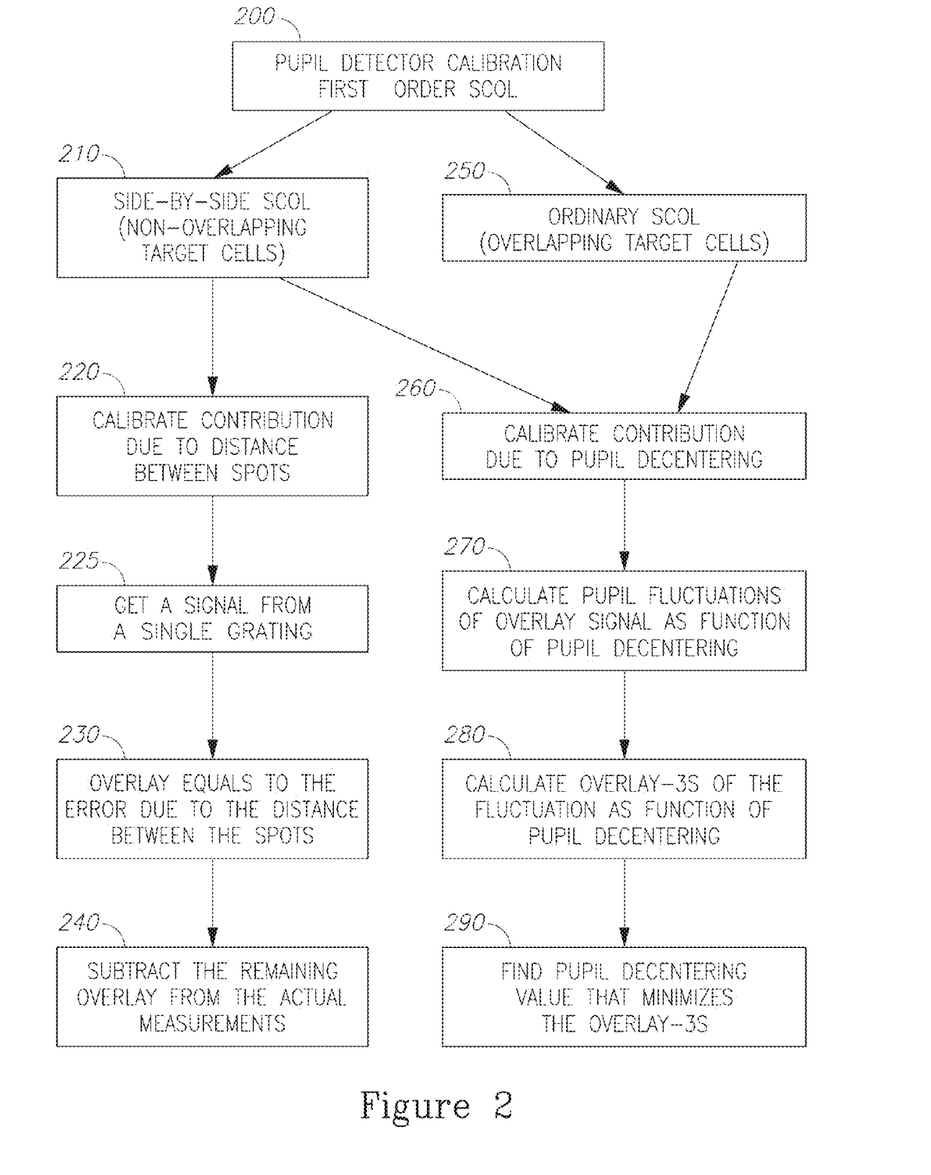
FIG. 2 is a high level schematic flowchart of a pupil plane calibration method for SCOL, according to some embodiments of the invention.

FIG. 2 is a high level schematic flowchart of a pupil plane calibration method 200 for SCOL, according to some embodiments of the invention. Following the development presented in Equations 1-6 above, method 200 comprises the following calibration procedures.

A first calibration procedure, which is specific for side-by-side SCOL targets 100B (stage 210) comprises calibrating $\overleftrightarrow{B}$ and $\Delta\vec{p}_{center}$ (stage 220) with a single grating. The side-by-side measurement procedure (disclosed e.g., in WIPO PCT Application No. PCT/US13/65527) is used to obtain a signal from a single grating instead of actual target 100B (stage 225). In this case, $\vec{A}(\vec{p})\cong 0$ as derived by setting (1)=g(2) in Equation 4 and $OVL_{real}=0$ as the single grating target clearly does not present any overlay. Thus, the remaining overlay signal is the term $$\frac{P}{2\pi}\vec{X}\cdot\overleftrightarrow{B}\cdot\Delta\vec{p}_{center}$$

of Equation 6, which can be measured (stage 230) as represented in Equation 7:

$$OVL(\vec{p},\vec{d},\overleftrightarrow{B}) = \frac{P}{2\pi}\vec{X}\cdot\overleftrightarrow{B}\cdot\Delta\vec{p}_{center}.\quad\text{Equation 7}$$

The overlay signal described in Equation 7 is recorded and subtracted from the overlay signals when one measures actual targets 100B (stage 240). It is noted that this last step is not applicable for the standard (grating-over-grating) SCOL targets, since the relative scaling and rotation of the pupil grid have no effect on the calculated OVL using such targets.

A first calibration procedure, which may be applied to calibrate $\vec{d}$ in side-by-side SCOL targets 100B (stage 210, after or before 240) and/or in SCOL targets 100A (stage 250). As $\vec{X}\cdot\overleftrightarrow{B}\cdot\Delta\vec{p}_{center}$ is independent of pupil coordinate (and null when using SCOL targets 100A), the pupil center may be calibrated in the following way (stage 260, in side-by-side SCOL, this does not requires one to calibrate $\overleftrightarrow{B}$ and $\Delta\vec{p}_{center}$ first).

First, method 200 comprises calculating the pupil fluctuations of the overlay signal given by the pupil average of the per-pixel overlay minus the pupil average, as expressed in Equation 8 (stage 270).

$$OVL(k,d)-(\langle OVL(\vec{p},\vec{d},\overleftrightarrow{B})\rangle) = \vec{d}\cdot(\vec{A}(\vec{q})-\langle A\vec{A}(\vec{q})\rangle)+\quad\text{Equation 8}$$

Denoting the 3 sigma value of these fluctuations by OVL3S, and using Equation 6, OVL3S can be expressed and calculated (stage 280) according to Equation 9.

$$OVL3S(\vec{d}) = 3|\vec{d}\cdot\hat{g}|\sqrt{VAR(\vec{A}(\vec{q})\cdot\hat{g})}+\quad\text{Equation 9}$$

In Equation 9, VAR $(\vec{A}(\vec{q})\cdot\hat{g})$ is the pupil weighted variance of $\vec{A}(\vec{q})\cdot\hat{g}$. Method 200 further comprises finding the value of $|\vec{d}\cdot\hat{g}|$ which minimizes OVL3S(d) as a good approximation for the pupil center (stage 290).

Examples

The following example comprises simulation results which demonstrate the validity of the assumptions presented above for side-by-side targets 100B, as expressed in Equations 1-6.

Figure 3A:
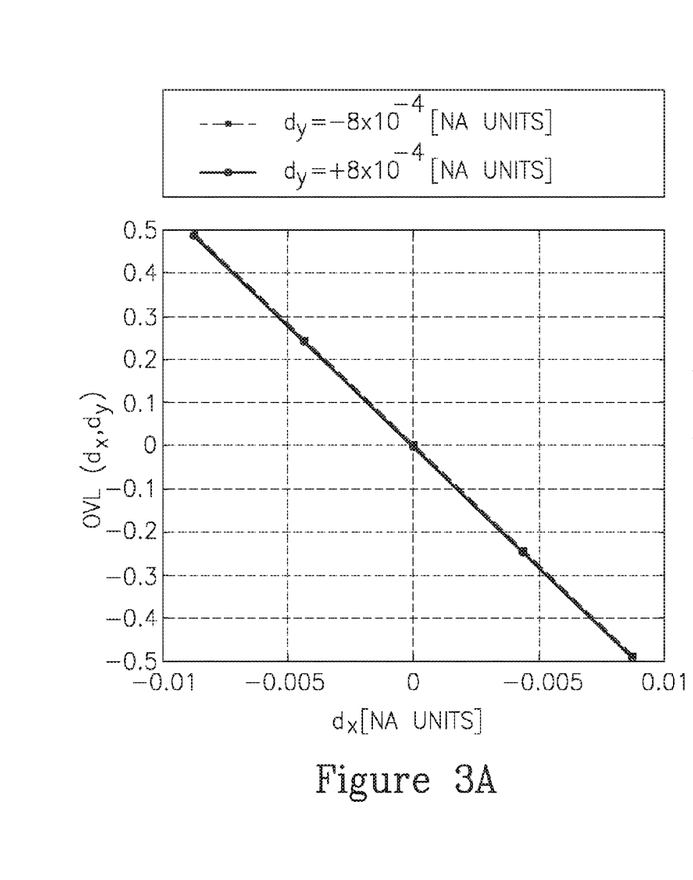
FIGS. 3A and 3B schematically illustrate a simulated dependency of the measured overlay on the misalignment vector for a side-by-side SCOL target, according to some embodiments of the invention.
Figure 3B:
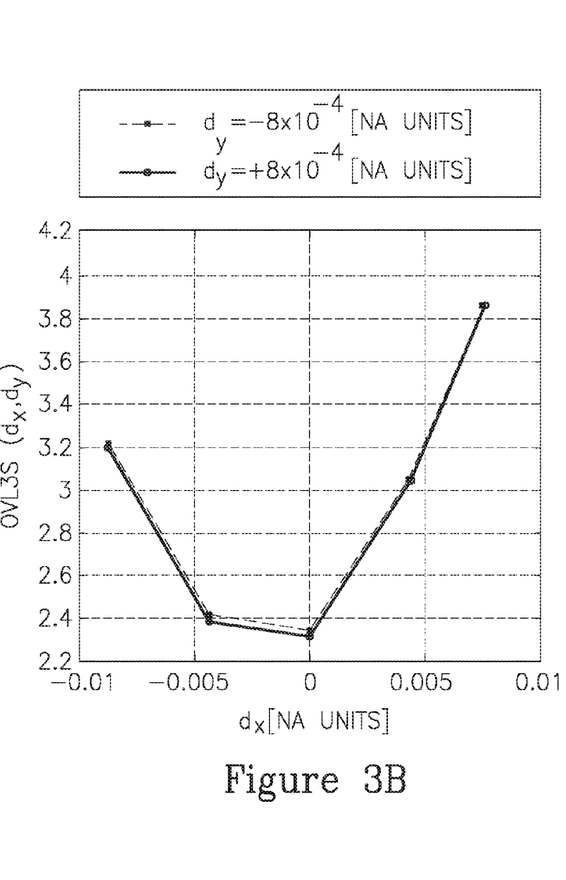

FIGS. 3A and 3B schematically illustrate a simulated dependency of the measured overlay on the misalignment vector for a side-by-side SCOL target, according to some embodiments of the invention. FIGS. 3A and 3B schematically illustrate a simulated dependency of the measured overlay for an X grating ($\hat{g}=\hat{x}$) along the x-axis (and its associated OVL3S) on the X and Y components of the misalignment vector $\vec{d}$($d_x$ and $d_y$) for a side-by-side SCOL target 100B. In the illustrated simulation, the top layer is a resist layer and the bottom layer is pattern silicon. The simulated overlay value was chosen in a non-limiting manner to be zero. These results focus on the calibration of $\vec{d}$, illustrated, without loss of generality, with $\vec{X}\cdot\overleftrightarrow{B}\cdot\Delta\vec{p}_{center}=0$. Clearly, the overlay error is linear in the decentering (FIG. 3A) and the overlay sensitivity to decentering is much more pronounced when $\vec{d}\|\hat{g}$ compared to the case where $\vec{d}\perp\hat{g}$. It is also evident that OVL3S reaches a minimum when $\vec{d}\cdot\hat{g}\cong 0$, i.e., $d_x=0$(FIG. 3B). The deviations of the simulation results from Equations 2 and 5 are due to finite-target size effects and to the leading order approximation done in Equations 1 and 2.

The following example comprises simulation results which demonstrate the validity of the assumptions presented above for SCOL targets 100A with overlapping target cells 105, as expressed in Equations 1-6.

Figure 4A:
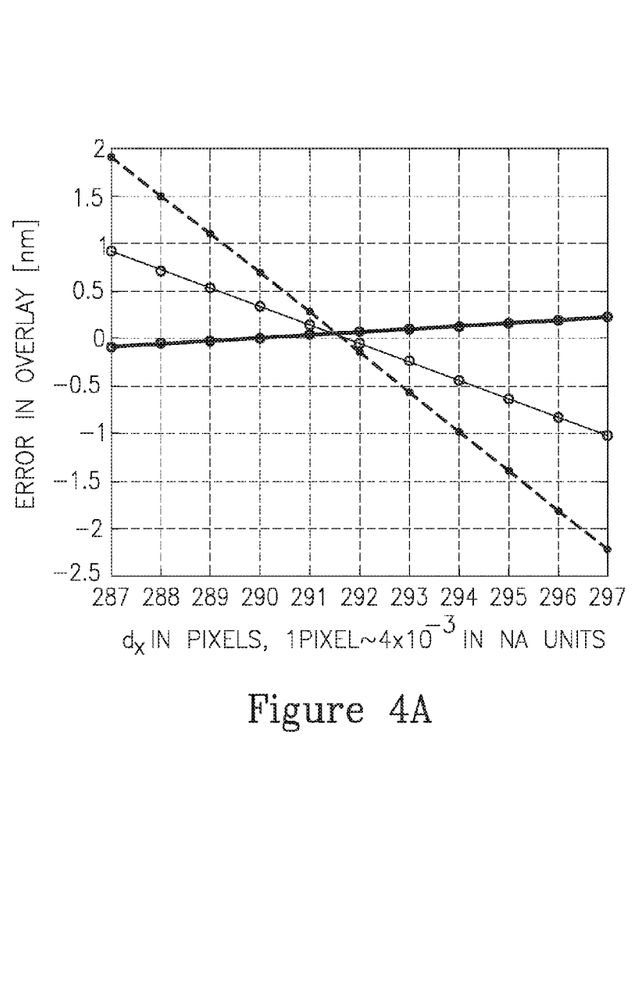
FIGS. 4A-4C schematically illustrate an experimentally measured dependency of the measured overlay on the misalignment vector for a standard SCOL target, according to some embodiments of the invention.
Figure 4B:
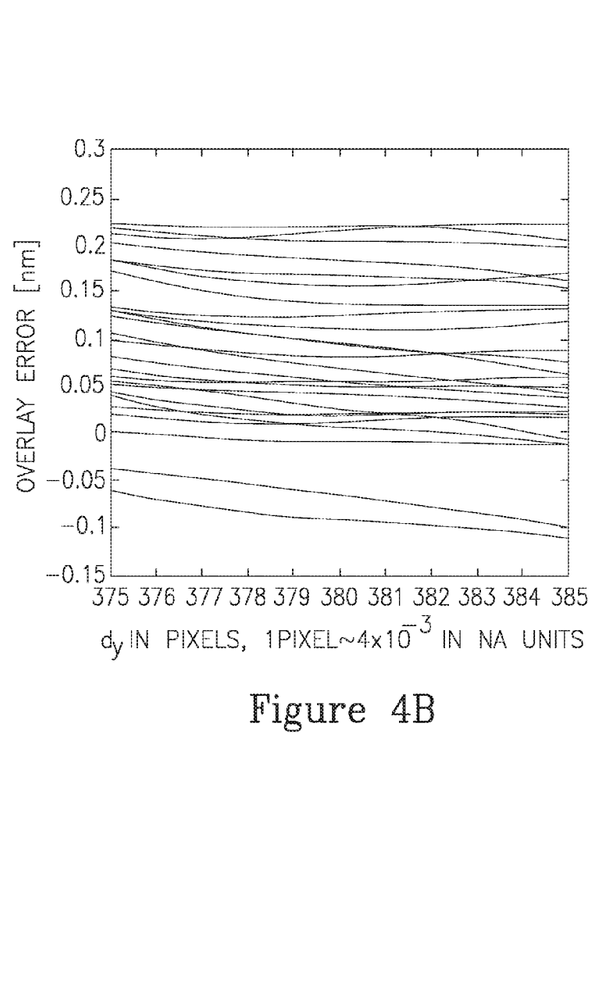
Figure 4C:
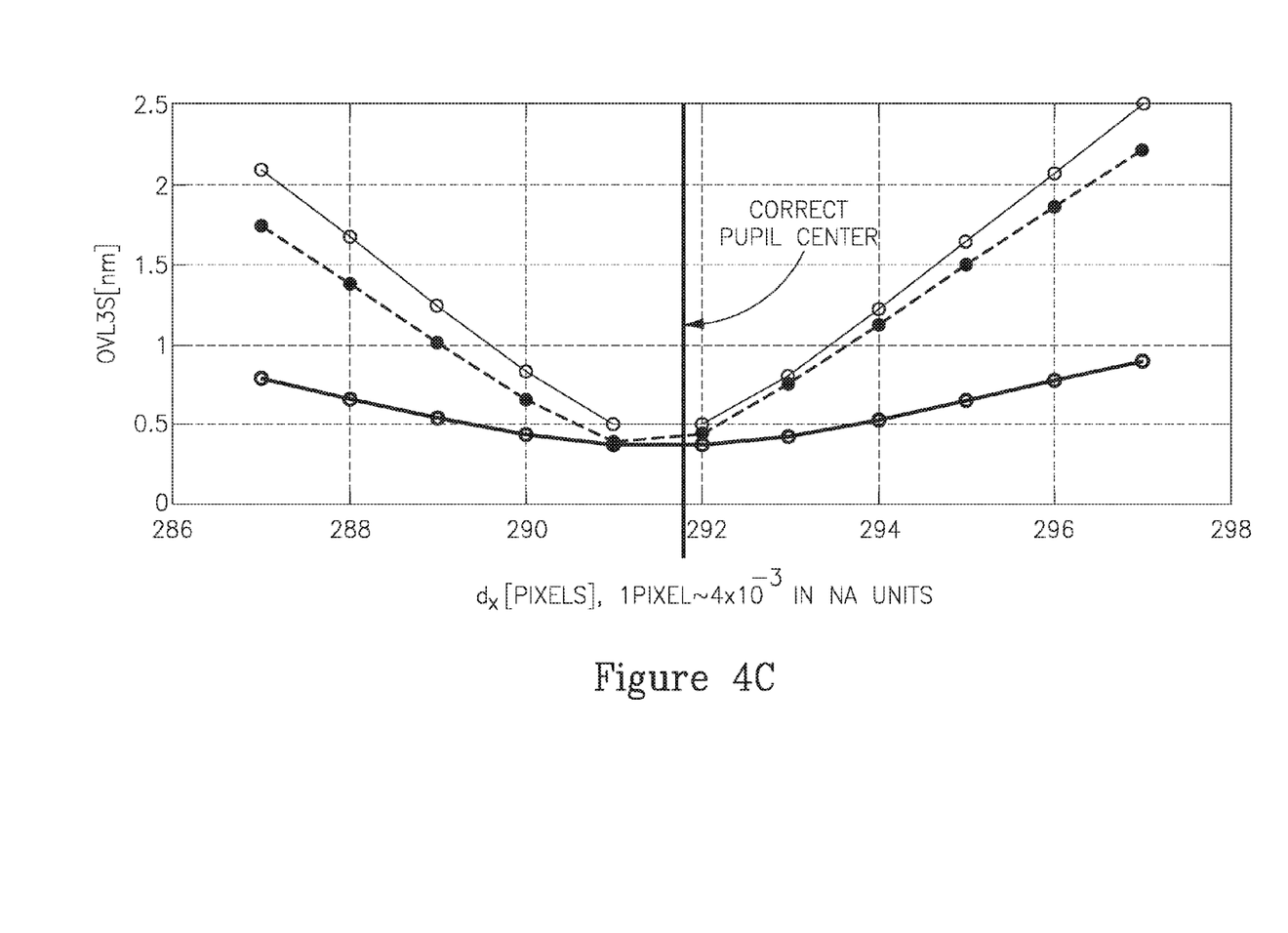

FIGS. 4A-4C schematically illustrate an experimentally measured dependency of the measured overlay on the misalignment vector for a standard SCOL target, according to some embodiments of the invention. The tested wafer had an upper layer of a patterned photoresist and a lower layer of patterned silicon. FIG. 4A-4D illustrate the influence of the changes induced by $\vec{d}$ on the OVL (FIGS. 4A and 4B) and on the OVL3S (FIG. 4C). FIG. 4A illustrates the overlay error from three different wafer sites versus $d_x$. FIG. 4B illustrates the overlay error from a multitude of wafer sites versus $d_y$. FIG. 4C illustrates the OVL3S from three different wafer sites versus $d_x$. An indication for the accuracy of the pupil calibration is given by an independent measurement of the correct pupil center by other means, which coincides with the result calculated by the disclosed method. It is noted that the sites measured in FIGS. 4A-4C are not the same in the different figures.

Figure 5:
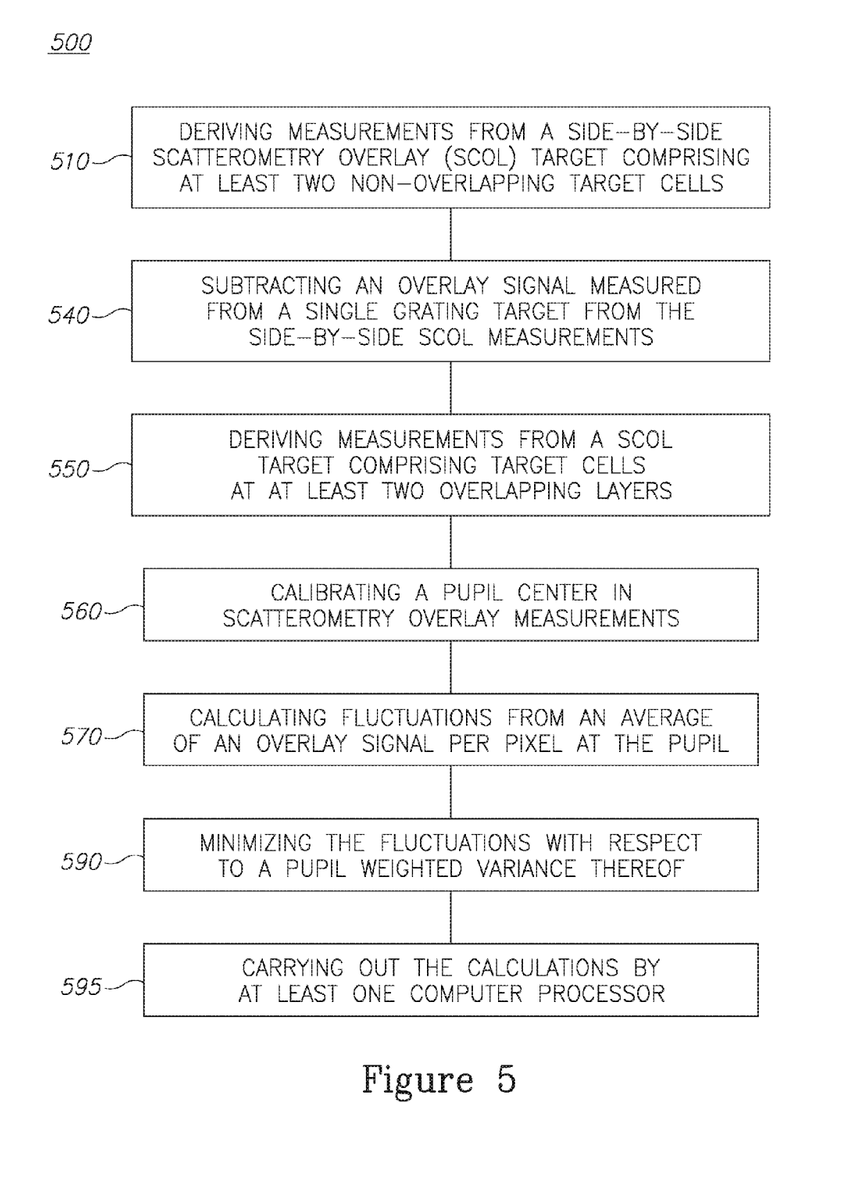
FIG. 5 is a high level flowchart illustrating a method, according to some embodiments of the invention.

FIG. 5 is a high level flowchart illustrating method 500, according to some embodiments of the invention. Any computational step of method 500 may be carried out by at least one computer processor (stage 595), and/or by implemented in software or hardware modules.

Method 500 comprises calibrating a pupil center in scatterometry overlay measurements (stage 560) by calculating fluctuations from first statistical figure of merit (e.g., an average, a weighted average, a median etc.) of an overlay signal per pixel at the pupil (stage 570) and significantly reducing (e.g., minimizing or substantially minimizing) the fluctuations with respect to a second statistical figure of merit, such as a pupil weighted variance of the fluctuations (stage 590). Any combination of the first and second figures of merit may be used, depending on specific calibration and measurement requirements.

Method 500 may comprise deriving the measurements from a scatterometry overlay (SCOL) target 100A comprising target cells 105 at least two overlapping layers (stage 550).

Method 500 may comprise deriving the measurements from a side-by-side SCOL target comprising at least two non-overlapping target cells (stage 510) and subtracting an overlay signal measured from a single grating target from the side-by side SCOL measurements (stage 540).

Method 500 comprises calibration techniques that are configured to reduce and/or eliminate the pupil calibration sensitivity of the overlay, TIS, and TIS3 S measurement. Method 500 comprises the first calibration procedure of pupil calibration of the center of the first order using a single grating calibration, and/or the second calibration procedure of pupil calibration of the center of pupil using overlay pupil information and a standard SCOL or side-by-side target. The second calibration procedure may be carried out independently of the first calibration procedure and/or be carried out before or after the first calibration procedure. The second calibration procedure may be carried out "on the fly" during the metrology measurements (in measurement mode) or in train mode, prior to actual metrology measurements.

Certain embodiments comprise a computer program product comprising a computer readable storage medium having computer readable program embodied therewith, the computer readable program configured to implement any of the stages of method 500.

Certain embodiments comprise a calibration module, possibly at least partially implemented in computer hardware, configured to calibrate a pupil center in scatterometry overlay measurements, by calculating fluctuations from a first statistical figure of merit (e.g., an average, a weighted average, a median etc.) of an overlay signal per pixel at the pupil and significantly reducing (e g minimizing) the fluctuations with respect to a second statistical figure of merit of the fluctuations (e.g., a pupil weighted variance of the fluctuations). The calibration module may be further arranged to derive the measurements from a scatterometry overlay (SCOL) target comprising target cells at least two overlapping layers. The calibration module may be further arranged to derive the measurements from a side-by-side SCOL target comprising at least two non-overlapping target cells. The calibration module may be further arranged to subtract an overlay signal measured from a single grating target from the side-by side SCOL measurements.

Advantageously, the disclosed methods reduce significantly and/or eliminate the sensitivity of the measurements of any of the overlay, TIS and TIS3S to possible errors in pupil coordinates such as those originating from pupil miscalibrations. The disclosed methods achieve the sensitivity reduction using signals that are, by definition, overlay signals, and that are very sensitive to the required calibration parameters, thereby improving the robustness of the misalignment correction; enable boosting the performance of pupil-calibration-related TIS and TIS3S; and enable the locating the pupil center in a way that can be performed on-the-fly, without requiring additional modeling.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:
1. A method of calibrating a pupil center in scatterometry overlay measurements, comprising:
acquiring one or more scatterometry overlay (SCOL) measurements via an overlay metrology tool;
calculating, with one or more processors, one or more fluctuations from a first statistical figure of merit of a per pixel overlay signal at a pupil plane of the overlay metrology tool based on the one or more SCOL measurements;
adjusting, with one or more processors, the one or more calculated fluctuations based on a second statistical figure of merit of the per pixel overlay signal at the pupil plane;
determining, with the one or more processors, a pupil calibration value that reduces the one or more adjusted fluctuations; and providing the determined pupil calibration value to calibrate one or more coordinates of one or more detectors located at the pupil center of the pupil plane of the overlay metrology tool.

2. The method of claim 1, wherein the first statistical figure of merit is an average and the second statistical figure of merit is a pupil weighted variance.

3. The method of claim 1, wherein the first statistical figure of merit is a pupil weighted average.

4. The method of claim 1, wherein the first statistical figure of merit is a median.

5. The method of claim 1, wherein the determining the pupil calibration value that reduces the one or more adjusted fluctuations comprises:
  determining the pupil calibration value that minimizes the one or more adjusted fluctuations.

6. The method of claim 1, wherein the acquiring the one or more SCOL measurements comprises:
  acquiring the one or more SCOL measurements from a SCOL target including one or more target cells at two or more overlapping layers.

7. The method of claim 1, wherein the acquiring the one or more SCOL measurements comprises:
  acquiring the one or more SCOL measurements from a side-by-side SCOL target including at least two non-overlapping target cells.

8. The method of claim 7, further comprising:
  acquiring one or more SCOL measurements from a single grating SCOL target; and
  subtracting the one or more SCOL measurements acquired from a single grating SCOL target from the one or more SCOL measurements acquired from the side-by-side SCOL target.

9. A system comprising:
  one or more processors configured to execute a set of computer readable program instructions, the set of computer readable program instructions configured to cause the one or more processors to:
    receive one or more scatterometry overlay (SCOL) measurements from an overlay metrology tool, wherein the overlay metrology tool is configured to acquire the one or more SCOL measurements from one or more SCOL targets;
    calculate one or more fluctuations from a first statistical figure of merit of a per pixel overlay signal at a pupil plane of the overlay metrology tool based on the received one or more SCOL measurements;
  adjust the one or more calculated fluctuations based on a second statistical figure of merit of the per pixel overlay signal at the pupil plane;
  determine a pupil calibration value that reduces the one or more adjusted fluctuations; and
  provide the determined pupil calibration value to calibrate one or more coordinates of one or more detectors located at the pupil center of the pupil plane of the overlay metrology tool.

10. A system comprising:
  an overlay metrology tool including one or more detectors located at a pupil center of a pupil plane, wherein the overlay metrology tool is configured to acquire one or more scatterometry overlay (SCOL) measurements from one or more SCOL targets;
  one or more processors configured to execute a set of computer readable program instructions, the set of computer readable program instructions configured to cause the one or more processors to:
    receive the one or more scatterometry overlay (SCOL) measurements from the overlay metrology tool;
    calculate one or more fluctuations from a first statistical figure of merit of a per pixel overlay signal at a pupil plane of the overlay metrology tool based on the received one or more SCOL measurements;
    adjust the one or more calculated fluctuations based on a second statistical figure of merit of the per pixel overlay signal at the pupil plane; and
    determine a pupil calibration value that reduces the one or more adjusted fluctuations; and
    provide the determined pupil calibration value to calibrate one or more coordinates of the one or more detectors located at the pupil center of the pupil plane of the overlay metrology tool.

11. The system of claim 10, wherein the first statistical figure of merit is an average and the second statistical figure of merit is a pupil weighted variance.

12. The system of claim 10, wherein the first statistical figure of merit is a pupil weighted average.

13. The system of claim 10, wherein the first statistical figure of merit is a median.

14. The system of claim 10, wherein the one or more processors are further configured to minimize the fluctuations.

15. The system of claim 10, wherein the overlay metrology tool is further configured to acquire the one or more SCOL measurements from the one or more SCOL targets, wherein the one or more SCOL targets comprise:
  a SCOL target including one or more target cells at two or more overlapping layers.

16. The system of claim 10, wherein the overlay metrology tool is further configured to acquire the one or more SCOL measurements from the one or more SCOL targets, wherein the one or more SCOL targets comprise:
  a side-by-side SCOL target including at least two non-overlapping target cells.

17. The system of claim 16, wherein the metrology tool is further configured to acquire one or more SCOL measurements from a single grating SCOL target, wherein the one or more processors are further configured to subtract the one or more SCOL measurements acquired from a single grating target from the one or more SCOL measurements acquired from the side-by-side SCOL target.

18. A method of calibrating a pupil center in scatterometry overlay measurements, comprising:
  acquiring one or more scatterometry overlay (SCOL) measurements from a side-by-side SCOL target including at least two non-overlapping target cells;
  acquiring one or more SCOL measurements from a single grating SCOL target;
  subtracting, with one or more processors, the one or more SCOL measurements acquired from a single grating SCOL target from the one or more SCOL measurements acquired from the side-by-side SCOL target;
  acquiring one or more SCOL measurements from a SCOL target including one or more target cells at two or more overlapping layers;
  determining a pupil calibration value; and
  providing the determined pupil calibration value to calibrate one or more coordinates of one or more detectors located at a pupil center of a pupil plane of an overlay metrology tool.

* * * * *